(12) United States Patent
Tanase et al.

(10) Patent No.: US 9,784,659 B2
(45) Date of Patent: Oct. 10, 2017

(54) MICROPARTICLE FRACTIONATING APPARATUS AND METHOD OF FRACTIONATING MICROPARTICLE

(71) Applicant: Sony Corporation, Tokyo (JP)

(72) Inventors: Hironobu Tanase, Tokyo (JP); Takayuki Itou, Kanagawa (JP); Toru Yata, Kanagawa (JP); Akiko Tsuji, Kanagawa (JP); Takashi Tago, Tokyo (JP)

(73) Assignee: Sony Corporation, Tokyo (JP)

(*) Notice: Subject to any disclaimer, the term of this patent is extended or adjusted under 35 U.S.C. 154(b) by 0 days.

(21) Appl. No.: 14/440,765

(22) PCT Filed: Oct. 3, 2013

(86) PCT No.: PCT/JP2013/005910
§ 371 (c)(1),
(2) Date: May 5, 2015

(87) PCT Pub. No.: WO2014/073156
PCT Pub. Date: May 15, 2014

(65) Prior Publication Data
US 2015/0285726 A1    Oct. 8, 2015

(30) Foreign Application Priority Data

Nov. 8, 2012   (JP) .................. 2012-246432

(51) Int. Cl.
*B03C 7/00*   (2006.01)
*G01N 15/14*  (2006.01)
(Continued)

(52) U.S. Cl.
CPC ............ *G01N 15/14* (2013.01); *B01L 3/0268* (2013.01); *B03C 7/003* (2013.01); *B03C 7/12* (2013.01);
(Continued)

(58) Field of Classification Search
CPC ............... G01N 15/14; G01N 15/1404; G01N 15/1406; G01N 15/1409; G01N 2015/149;
(Continued)

(56) References Cited

U.S. PATENT DOCUMENTS 3,826,364 A * 7/1974 Bonner ................. B07C 5/3425
                                                              209/3.1
4,168,460 A    9/1979 Menke
(Continued)

FOREIGN PATENT DOCUMENTS

JP    53-013263      2/1978
JP    56-030870 A    3/1981
(Continued)

*Primary Examiner* — Joseph C Rodriguez
(74) *Attorney, Agent, or Firm* — Wolf, Greenfield & Sacks, P.C.

(57) ABSTRACT

Described are microparticle fractionating apparatus and methods of fractionating microparticles. Multiple electrodes may be used to charge droplets when separating and collecting microparticles based on a result analyzed by an optical methodologies. A first electrode may be used to charge a sample fluid, and a second electrode used to apply additional charge near a droplet break-off point.

18 Claims, 8 Drawing Sheets

(51) Int. Cl.
*B01L 3/02* (2006.01)
*B03C 7/12* (2006.01)
*B07C 5/02* (2006.01)
*B07C 5/344* (2006.01)
*G01N 15/10* (2006.01)
*B01L 3/00* (2006.01)

(52) U.S. Cl.
CPC ............ *B07C 5/02* (2013.01); *B07C 5/344* (2013.01); *G01N 15/1459* (2013.01); *G01N 15/1484* (2013.01); *B01L 3/5027* (2013.01); *B01L 2200/0652* (2013.01); *B01L 2300/0816* (2013.01); *B01L 2400/027* (2013.01); *B01L 2400/0415* (2013.01); *B01L 2400/0487* (2013.01); *G01N 2015/1006* (2013.01); *G01N 2015/1081* (2013.01); *G01N 2015/149* (2013.01)

(58) Field of Classification Search
CPC ......... B07C 5/342; B07C 5/3425; B03C 7/00; B03C 7/003; B03C 7/12; B01L 2200/0652; B01L 2400/027
See application file for complete search history.

(56) References Cited

U.S. PATENT DOCUMENTS

| | | | | |
|---|---|---|---|---|
| 4,284,496 A * | 8/1981 | Newton | ............... | G01N 1/28 209/127.1 |
| 4,325,483 A * | 4/1982 | Lombardo | ......... | G01N 15/1404 209/3.1 |
| 4,987,539 A * | 1/1991 | Moore | ............... | B07C 5/3427 209/579 |
| 5,080,770 A * | 1/1992 | Culkin | ............... | B01D 61/425 204/516 |
| 5,483,469 A * | 1/1996 | Van den Engh | ....... | G01N 15/14 209/3.1 |
| 5,776,781 A * | 7/1998 | Vardanega | ............... | B01L 1/04 209/3.1 |
| 6,589,792 B1 | 7/2003 | Malachowski | .... | G01N 15/1404 209/127.4 |
| 6,861,265 B1 * | 3/2005 | den Engh | ........ | G01N 15/1404 324/71.4 |
| 7,639,358 B2 * | 12/2009 | Kanda | ............... | G01N 15/1459 356/337 |
| 7,691,636 B2 * | 4/2010 | Frazier | ............... | G01N 15/1404 209/127.4 |
| 7,880,108 B2 * | 2/2011 | Schembri | ........... | G01N 15/1459 209/128 |
| 8,246,805 B2 * | 8/2012 | Shinoda | ............... | B01F 3/0819 204/451 |
| 8,748,183 B2 * | 6/2014 | Durack | ............... | C12N 5/0612 422/73 |
| 9,029,724 B2 | 5/2015 | Hashimoto et al. | | |
| 9,087,371 B2 * | 7/2015 | Muraki | ............... | G01N 15/1484 |
| 9,339,823 B2 | 5/2016 | Muraki et al. | | |
| 9,429,276 B2 * | 8/2016 | Katsumoto | ............... | F17D 1/00 |
| 9,588,036 B2 * | 3/2017 | Shinoda | ............... | B01L 3/0268 |
| 2007/0102634 A1 * | 5/2007 | Frey | ............... | H01J 49/0045 250/288 |
| 2008/0050283 A1 * | 2/2008 | Chou | ............... | B01L 3/5027 422/400 |
| 2008/0289966 A1 * | 11/2008 | Voldman | ............... | B03C 5/005 204/643 |
| 2011/0284378 A1 * | 11/2011 | Shinoda | ............... | B01L 3/0268 204/603 |
| 2012/0084022 A1 * | 4/2012 | Giovangrandi | ........... | G01F 1/58 702/45 |
| 2012/0247231 A1 * | 10/2012 | Kery | ............... | G01N 15/1031 73/863.21 |
| 2013/0256136 A1 | 10/2013 | Muraki et al. | | |
| 2013/0256197 A1 * | 10/2013 | Katsumoto | ............. | B03C 5/026 209/127.1 |
| 2013/0258075 A1 | 10/2013 | Muraki et al. | | |
| 2014/0087453 A1 | 3/2014 | Tahara | | |
| 2014/0097129 A1 * | 4/2014 | Foster | ............... | B01L 3/502761 209/579 |
| 2014/0144817 A1 | 5/2014 | Hashimoto et al. | | |
| 2014/0193059 A1 | 7/2014 | Muraki | | |
| 2014/0208875 A1 | 7/2014 | Muraki | | |
| 2014/0346047 A1 * | 11/2014 | Shinoda | ............... | B01L 3/0268 204/603 |
| 2015/0057787 A1 | 2/2015 | Muraki et al. | | |
| 2015/0068957 A1 | 3/2015 | Otsuka et al. | | |
| 2015/0204774 A1 | 7/2015 | Ito | | |
| 2015/0285727 A1 | 10/2015 | Muraki | | |
| 2015/0377763 A1 | 12/2015 | Brun et al. | | |
| 2016/0223451 A1 | 8/2016 | Muraki et al. | | |
| 2016/0245736 A1 | 8/2016 | Muraki et al. | | |
| 2016/0266027 A1 | 9/2016 | Muraki et al. | | |

FOREIGN PATENT DOCUMENTS

| | | |
|---|---|---|
| JP | 62-167478 A | 7/1987 |
| JP | 11-501258 A | 2/1999 |
| JP | 2002-505423 A | 2/2002 |
| JP | 2007-532874 A | 11/2007 |
| JP | 2010-190680 A | 9/2010 |
| JP | 2011-237201 A | 11/2011 |

* cited by examiner

[Fig. 1]
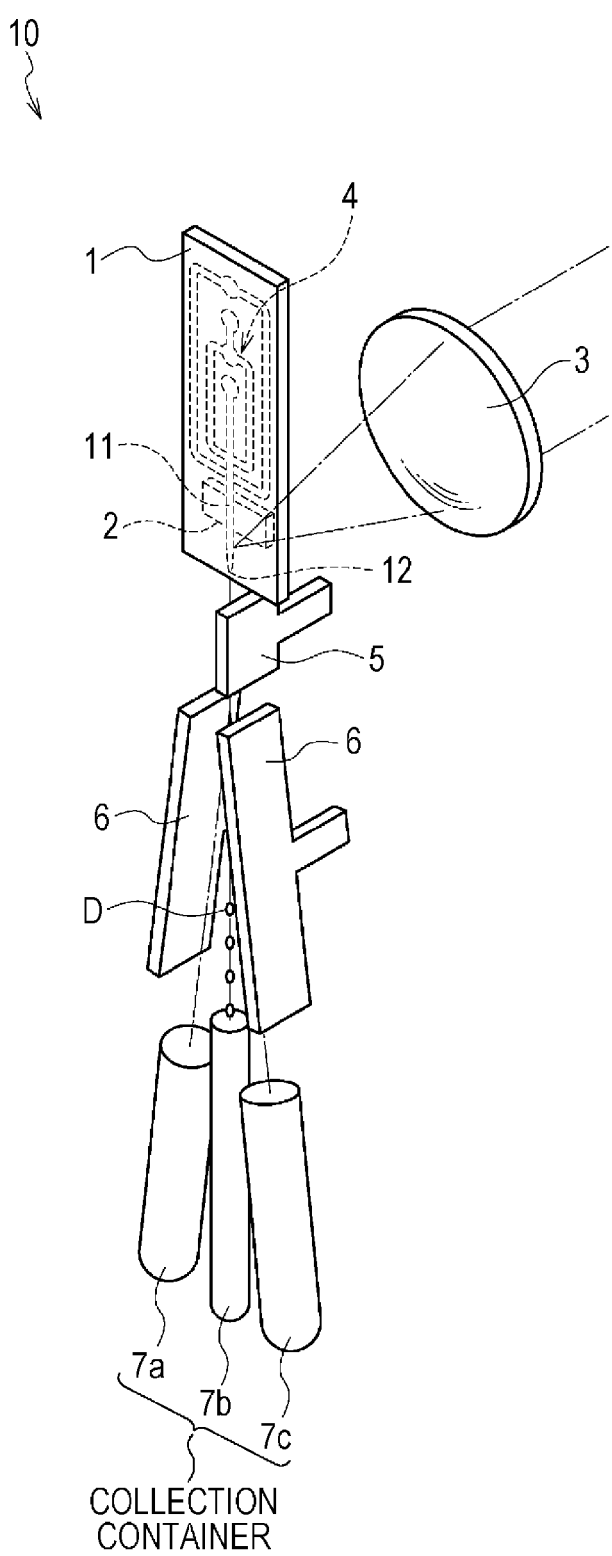

[Fig. 2A]
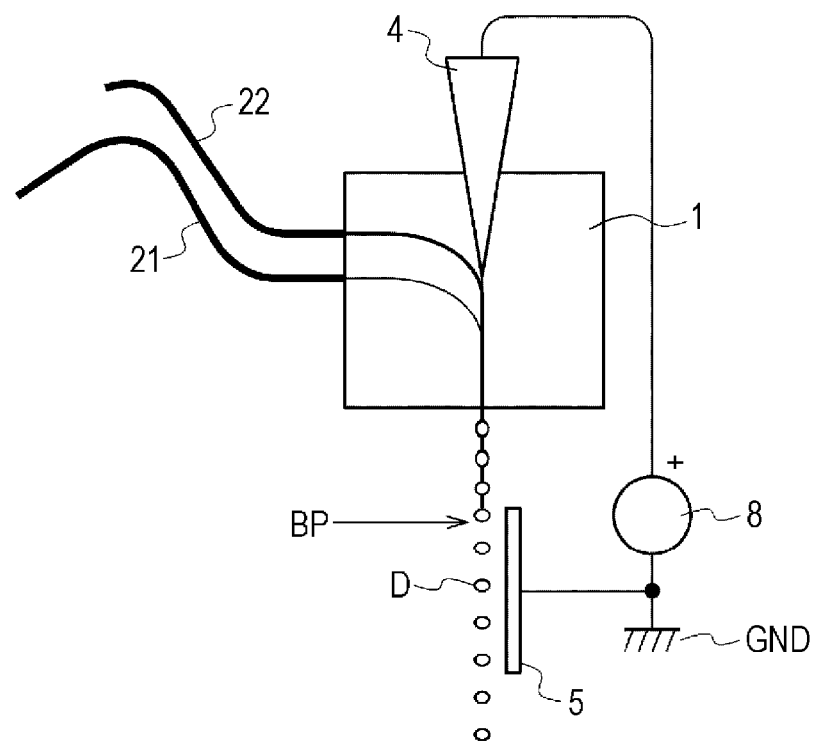
[Fig. 2B]
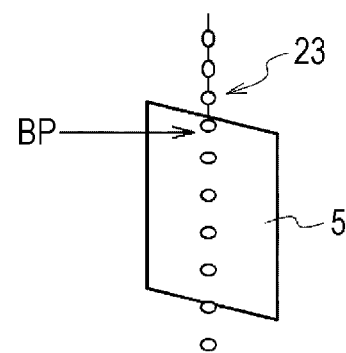

[Fig. 3A]
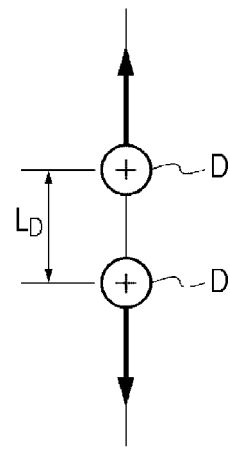
[Fig. 3B]
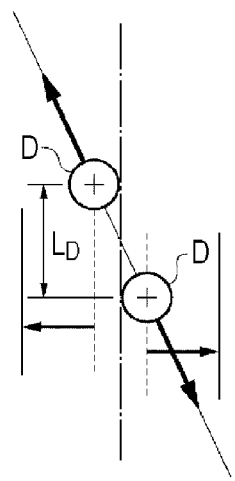
[Fig. 3C]
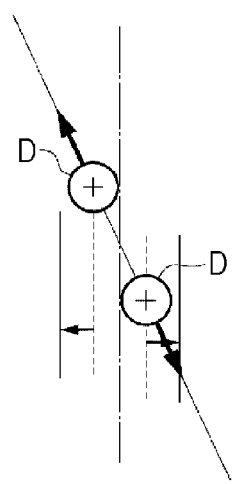

[Fig. 4]
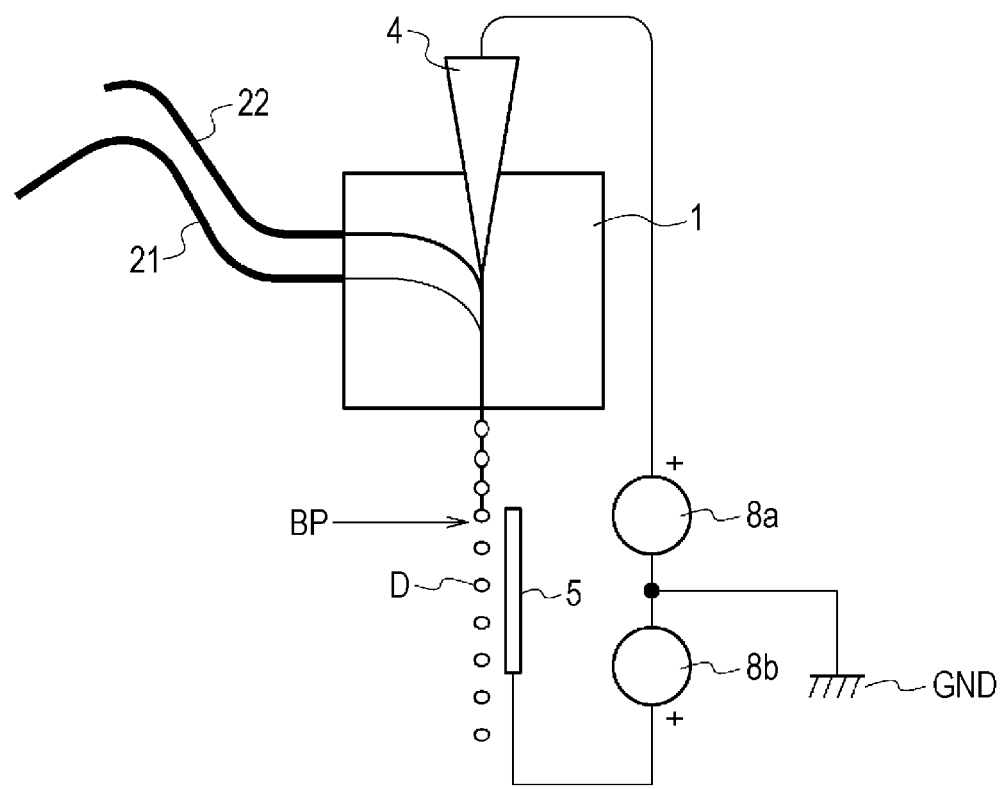

[Fig. 5A]
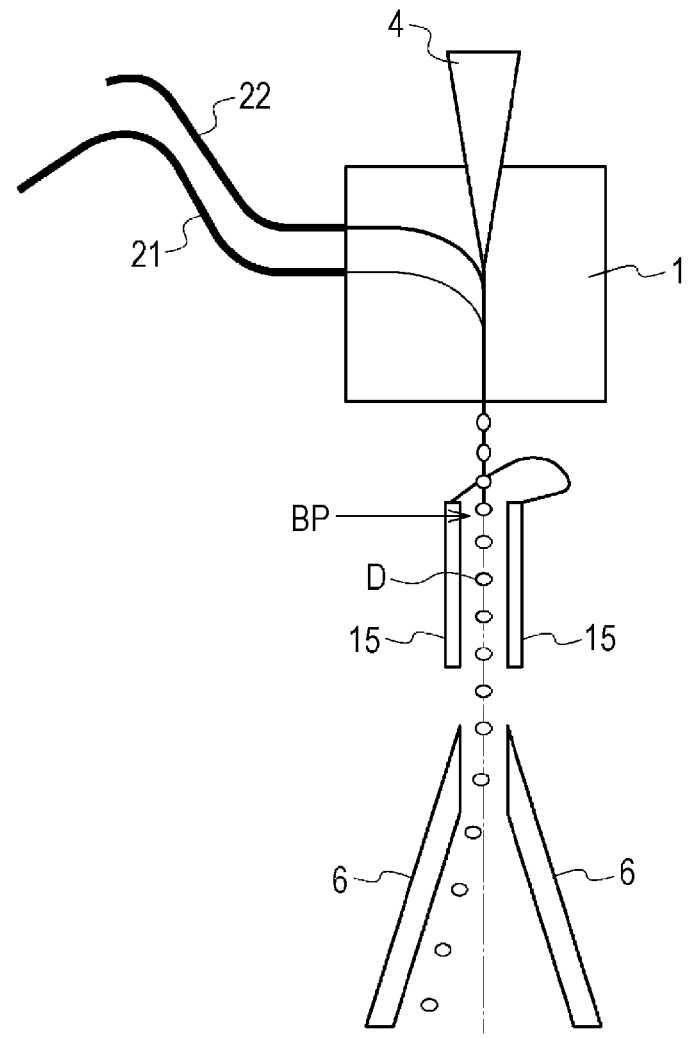
[Fig. 5B]
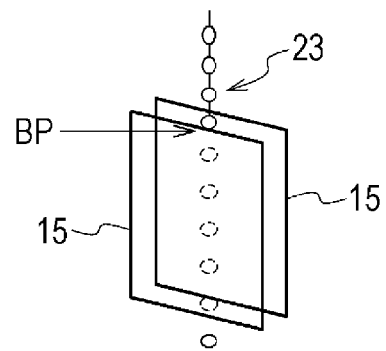

[Fig. 6A]
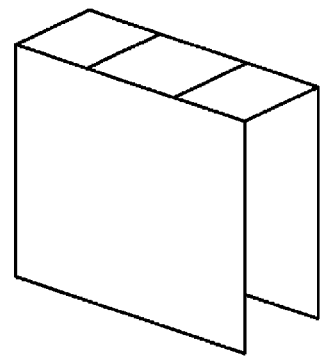
[Fig. 6B]
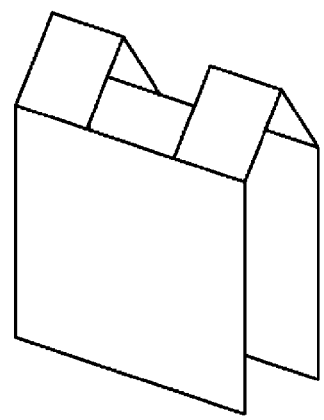

[Fig. 7A]
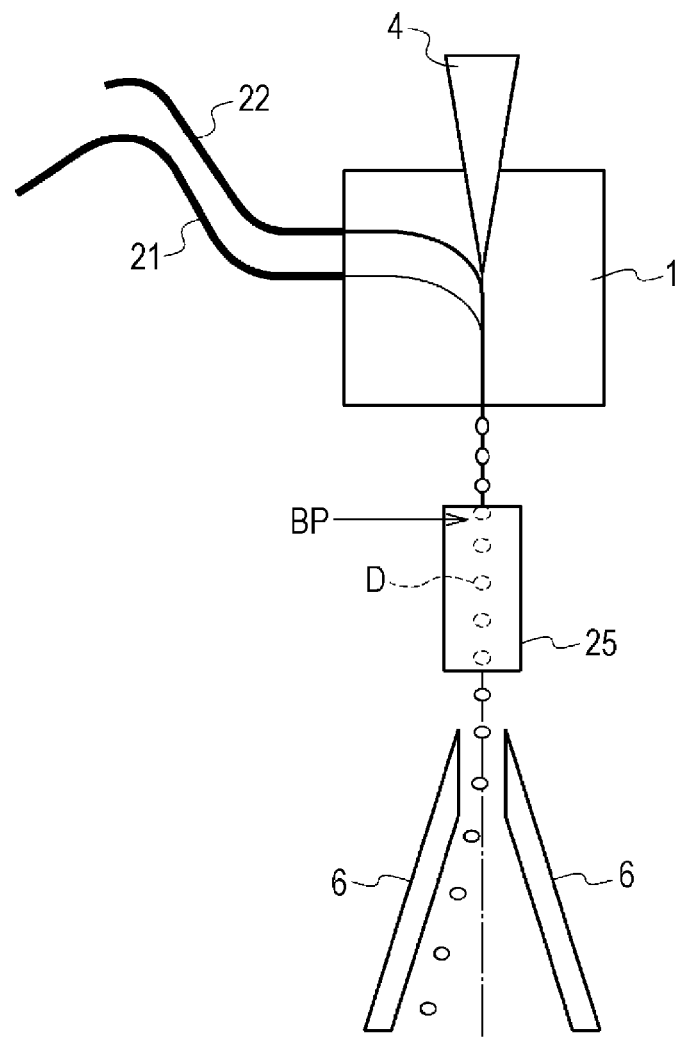
[Fig. 7B]
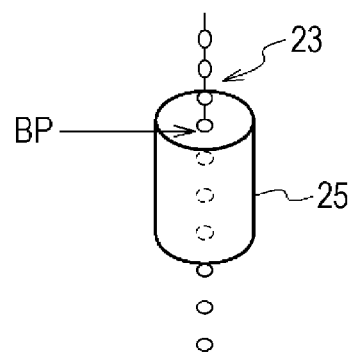

[Fig. 8A]
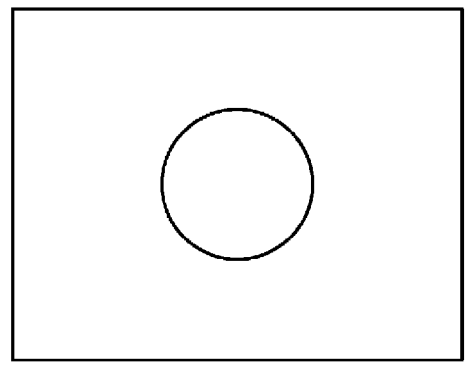
[Fig. 8B]
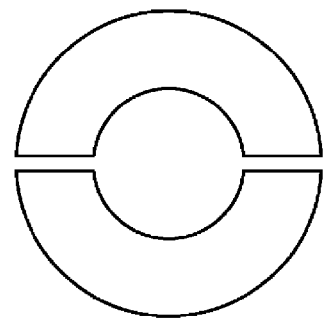

MICROPARTICLE FRACTIONATING APPARATUS AND METHOD OF FRACTIONATING MICROPARTICLE

CROSS REFERENCE TO RELATED APPLICATIONS

This is a U.S. National Stage Application under 35 U.S.C. §371, based on International Application No. PCT/JP2013/005910, filed Oct. 3, 2013, which claims priority to Japanese Patent Application JP 2012-246432, filed Nov. 8, 2012.

TECHNICAL FIELD

The present technology relates to a microparticle fractionating apparatus and a method of fractionating microparticles. More specifically, the present technology relate to a technology that gives charges to droplets when separating and collecting microparticles based on a result analyzed by an optical methodology and the like.

BACKGROUND ART

In the related art, an optical measurement using flow cytometry (flow cytometer) has been used for an analysis of biological microparticles such as a cell, a microorganism and a liposome. The flow cytometer is an apparatus that radiates light to microparticles passing through a flow path formed in a flow cell or a micro chip, and the like, detects fluorescence or scattered light emitted from the individual microparticles, and analyzes the detected result.

The flow cytometer includes a function of separating and collecting only microparticles having specific characteristics, and particularly, a microparticle apparatus targeting a cell as an object to be fractionated is referred to as a "cell sorter". The cell sorter generally employs a droplet charging method that charges and separates droplets containing the microparticles as a fractionation method (refer to PTLs 1 to 3).

For example, in the flow cytometer described in PTL 1, a charging ring is disposed at a position (break-off-point) where droplets are separated from a carrier fluid and charges are selectively given to the droplets of the object to be fractionated. Further, a travelling direction of the charged droplets is changed by a droplet deflection plate disposed downstream from the charging ring, and the charged droplets are collected in predetermined containers or the like.

On the other hand, in the microparticle fractionating apparatus described in PTL 2, a microtube for introducing a sample liquid to an interior of a sheath liquid laminar flow is configured of a metal, and positive or negative charges is given to a sheath liquid and a sample liquid which pass through the interior of the flow path by applying a voltage to the microtube. In addition, in the microparticle fractionating apparatus described in PTL 3, a charging electrode is provided in a portion of the flow path provided in a microchip. Furthermore, in the microparticle fractionating apparatus described in PTLs 2 and 3, a ground electrode is disposed between an orifice and an electrode (droplet deflection plate) in order to eliminate influence of high potential of the electrode pair changing the travelling direction of the droplets.

CITATION LIST

Patent Literature

PTL 1: Japanese Unexamined Patent Application Publication (Translation of PCT Application) No. 2007-532874

PTL 2: Japanese Unexamined Patent Application Publication No. 2010-190680

PTL 3: Japanese Unexamined Patent Application Publication No. 2011-237201

SUMMARY

Technical Problem

However, in the above-described droplet charging method of the related art of PTLs 1 to 3, since it is difficult to constantly maintain an amount of charge given to the droplets and a fluid stream (flow of droplet) is blurred during the fractionation, there is a problem that sorting is not stable.

Therefore, in the present technology, it is desirable to provide a microparticle fractionating apparatus and a method of fractionating microparticles which realizes stable sorting.

Solution to Problem

Various apparatus and methods for fractionating microparticles are contemplated. According to some embodiments, a charging apparatus for charging droplets discharged from an orifice of a microparticle fractionating apparatus comprises a first electrode configured to apply a first bias from a bias source to a sample liquid supplying the orifice, and a second electrode configured to apply a second bias from the bias source to the droplets formed from the sample liquid. The second bias may be referenced to the first bias, and the second electrode may be located at a droplet break-off-point near the orifice.

In some embodiments, a microparticle fractionating apparatus comprises a droplet-forming device having an orifice and arranged to receive a sample liquid containing microparticles and produce a stream of separated droplets. The microparticle fractionating apparatus may further comprise a first electrode configured to apply a first bias from a bias source to the sample liquid supplying the orifice, and a second electrode configured to apply a second bias from the bias source to the separated droplets formed from the sample liquid. The second bias may be referenced to the first bias, and the second electrode may be located at a droplet break-off-point near the orifice. The microparticle fractionating apparatus may further comprise deflection plates located after the second electrode and arranged to subject the separated droplets to an electric field so as to deflect the paths of the separated droplets.

According to some embodiments, a method for charging droplets discharged from an orifice of a microparticle fractionating apparatus may include acts of applying a first bias from a bias source to a first electrode arranged to be in contact with a sample liquid supplying the orifice that is arranged to produce the droplets, referencing a second bias from the bias source to the first bias, and applying the second bias to a second electrode located at a droplet break-off-point near the orifice.

Advantageous Effects of Invention

According to the present technology, since electrodes for charging are also provided at a droplet-making position in addition to a flow path, an amount of charge given to a droplet becomes constant, and it is possible to stabilize sorting.

BRIEF DESCRIPTION OF DRAWINGS

FIG. 1 is a view illustrating a schematic configuration of a microparticle fractionating apparatus according to a first embodiment of the present technology.

FIG. 2A is a view schematically illustrating operation of the microparticle fractionating apparatus 10 illustrated in FIG. 1.

FIG. 2B is a view illustrating a positional relation between a BP (break-off-point) and a second charging electrode 5.

FIG. 3A is a schematic view illustrating an ideal droplet array state.

FIG. 3B is a schematic view illustrating the droplet array state in a case where the second charging electrode 5 is not disposed.

FIG. 3C is a schematic view illustrating the droplet array state in a case where the second charging electrode 5 is disposed.

FIG. 4 is a view schematically illustrating the operation of the microparticle fractionating apparatus of a modified example of the first embodiment of the present technology.

FIG. 5A is a view schematically illustrating the operation of the microparticle fractionating apparatus of a second embodiment of the present technology.

FIG. 5B is a view illustrating the positional relation between the break-off-point and the second charging electrode.

FIG. 6A is a perspective views illustrating another embodiment of a parallel plate electrode.

FIG. 6B is a perspective view illustrating another embodiment of a parallel plate electrode.

FIG. 7A is a view schematically illustrating the operation of the microparticle fractionating apparatus of a third embodiment of the present technology.

FIG. 7B is a view illustrating the positional relation between the break-off-point and the second charging electrode.

FIG. 8A is a plan view illustrating another embodiment of the second charging electrode.

FIG. 8B is a plan view illustrating another embodiment of the second charging electrode.

DESCRIPTION OF EMBODIMENTS

Hereinafter, detailed description will be given with regard to an embodiment for carrying out the present technology with reference to the accompanying drawings. Moreover, the present technology is not limited to respective embodiments described below. In addition, description will be given in the following order.

1. A first embodiment
(Example of a microparticle fractionating apparatus in which a plate electrode is disposed at a break-off-point)
2. A modified example of the first embodiment
(Example of the microparticle fractionating apparatus in which AC pulse voltages having different polarities are applied to respective electrodes)
3. A second embodiment
(Example of the microparticle fractionating apparatus in which a parallel plate electrode is disposed at the break-off-point)
4. A third embodiment
(Example of the microparticle fractionating apparatus in which a circular hole electrode is disposed at the break-off-point)

1. First Embodiment

First, description will be given with regard to the microparticle fractionating apparatus according to the first embodiment of the present technology. FIG. 1 illustrates a schematic configuration of the microparticle fractionating apparatus of the first embodiment of the present technology. In addition, FIG. 2A is a view schematically illustrating operation of a microparticle fractionating apparatus 10 illustrated in FIG. 1, and FIG. 2B is a view illustrating a positional relation between a BP (break-off-point) and a second charging electrode 5.

<Overall Configuration of Apparatus>

As illustrated in FIG. 1, the microparticle fractionating apparatus 10 of the present embodiment includes a microchip 1, a vibration device 2, a light detection unit 3, a charging unit which is configured with a first charging electrode 4 and a second charging electrode 5, a deflection plate 6, and collection containers 7a to 7c.

<With Regard to Microparticle>

In the microparticles analyzed and fractionated by the microparticle fractionating apparatus 10 of the present embodiment, a biological microparticle such as a cell, a microorganism, a ribosome, and a synthetic particle such as a latex particle and a gel particle, and an industrial particle are widely included.

In biological microparticles, a chromosome, a ribosome, a mitochondria, an organelle (cell minute organ) and the like are included. In addition, in cells, a plant cell, an animal cell, and hematopoietic cell are included. Furthermore, in the microorganisms, bacteria such as an *Escherichia coli* and the like, viruses such as a tobacco mosaic virus and the like, fungi such as yeast and the like are included. In the biological microparticles, nucleic acid or protein, and biological polymers, and complexes of the biological polymers may also be included.

On the other hand, as an example of an industrial particle, there is an organic polymeric material, an inorganic material, or a metal material. As an organic polymer material, it is possible to use polystyrene, styrene-divinylbenzene copolymer, and polymethyl methacrylate, and the like. In addition, as an inorganic material, it is possible to use glass, silica, and a magnetic material, and the like. As a metal material, for example, it is possible to use gold colloid, and aluminum, and the like. Moreover, the shapes of these microparticles are generally spherical, but may be non-spherical, and the size and mass are not particularly limited.

<Microchip 122

In the microchip 1, a sample inlet in which a liquid 21 (sample liquid) containing microparticles targeted to be fractionated is introduced, a sheath inlet in which a sheath 22 is introduced, and an electrode inlet in which a first charging electrode 4 immersed in the sheath liquid is inserted are formed. Further, the sheath liquid 22 introduced in the sheath inlet joins the sample liquid 21 in a sample flow path 11 via the charging electrode inlet, and is discharged from an orifice 12.

It is possible to form the microchip 1 with glass or various plastics (PP, PC, COP, PDMS, and the like). The material of the microchip 1 can preferably be a material which has transparency with respect to measuring light radiated from a light detection unit 3 and has less optical error since wavelength dispersion is small.

It is possible to form the microchip 1 by wet-etching or dry-etching the glass substrate and by nano-imprinting, injection molding, or machining a plastic substrate. It is possible to form the microchip 1 by sealing a substrate in which the sample flow path 11 is formed on a substrate made of the same material or a different material.

<Vibration Device 2>

The vibration device 2 is provided at a position in contact with a portion of the microchip 1. The vibration device 2 vibrates the microchip 1, at a predetermined frequency, for example, which discharges the sample liquid and the sheath liquid from the orifice 12 into a space outside the chip where the sample liquid 21 and the sheath liquid 22 form into droplets D. A piezoelectric device and the like can be used as the vibration device 2, for example.

<Detection Unit 3>

The detection unit 3 radiates light (measuring light) to a predetermined portion of the sample flow path 11, and then detects the light (light to be measured) generated from the microparticles flowing through the sample flow path 11. The light detection unit 3 can be configured similarly to a flow cytometry of the related art. Specifically, the light detection unit is configured of a laser light source radiation system constituted by a condenser lens or a dichroic minor or a bandpass filter which collects and radiates laser light with respect to the microparticles, and a detection system that detects the light to be measured which is generated from the microparticles by radiation of the laser light.

The detection system, for example, is configured of area imaging device such as PMT (Photo Multiplier Tube) or CCD or CMOS device, and the like. Moreover, FIG. 1 illustrates only a condenser lens as the light detection unit 3. In addition, FIG. 3A to FIG. 3C illustrate cases where the radiation system and the detection system are configured of the same optical path, but the radiation system and the detection system may be configured of separate optical paths.

The light to be measured which is detected by the detection system of the light detection unit 3 is the light generated from the microparticles by radiation of the measuring light, for example, and can be scattered light such as forward-scattered light, side-scattered light, Rayleigh scattering, or Mie scattering, or fluorescence. The light to be measured is converted into electrical signals, and then the optical characteristics of the microparticles are detected by the electrical signals.

<Charging Unit>

The charging unit gives positive or negative charges to droplets D discharged from the orifice 12, and is configured of the first charging electrode 4, the second charging electrode 5, and a voltage source 8 applying predetermined voltages thereto. The first charging electrode 4 is disposed to be in contact with the sheath liquid and/or the sample liquid which flow through the flow path, and gives charges to the sheath liquid 22 and the sample liquid 21, for example, and is inserted to a charging electrode inlet of the microchip 1. In addition, a first voltage $V_1$ is applied to the first charging electrode 4 by the voltage source 8.

Moreover, in FIG. 1 and FIG. 2A, the first charging electrode 4 is disposed so as to be in contact with the sheath liquid 22, but the present technology is not limited thereto, and may be disposed so as to be in contact with the sample liquid 21 or may be disposed so as to be in contact with both the sample liquid 21 and the sheath liquid 22. However, considering the effect of the object to be fractionated on a cell, it is preferable that the first charging electrode 4 be disposed so as to be in contact with the sheath liquid 22.

On the other hand, the second charging electrode 5 is disposed in the vicinity of the BP (break-off-point) position in which the liquid discharged from the orifice 12 is made into droplets, and gives charges to the droplets D at least at the BP (break-off-point). The second charging electrode 5, for example, can be configured of a plate electrode. In addition, the second voltage $V_2$ different from the first voltage $V_1$ is applied to the second charging electrode 5 from the voltage source 8.

Here, the second charged voltage 5, at least at the BP (break-off-point), may be disposed at a position where charges can be given to the droplets D, further, may also extend upstream and/or downstream from the BP (break-off-point). However, in a case of giving charges upstream from the BP (break-off-point), there is a case where the effect is not sufficiently obtained by diffusion or degradation of the charges.

On the other hand, if giving the charges downstream from the BP (break-off-point), the droplets D are less likely to recombine. Therefore, it is desirable that the second charging electrode 5 extend to the position of 30 mm downstream in the traveling direction of the droplets D from the BP (break-off-point). Thus, it is possible to improve sorting accuracy.

In addition, it is desirable that the second charging electrode 5 be disposed at the position of less than or equal to 5 mm from a fluid stream 23 discharged from the orifice 12. Thus, it is possible to efficiently give charges to the droplets D.

<Deflection Plate 6>

The deflection plates 6 change the travelling direction of respective droplets D in the fluid stream 23 from an electric force acting between the electrodes given to the droplets D, and are opposed downstream from the second charging electrode 5 across the fluid stream 23. In the deflection plates 6, for example, it is possible to use a commonly-used electrode.

<Collection Container 7a to 7c>

Collection containers collect the droplets which pass through between the deflection plates 6, and it is possible to use a general-purpose plastic tube or a glass tube for experimental purpose. It is preferable that the collection containers 7a to 7c be interchangeably disposed within the apparatus. In addition, among the collection containers 7a to 7c, a drainage path of the collected droplets may be connected to a container which receives non-targeted microparticles.

Moreover, the number of the collection containers disposed in the microparticle fractionating apparatus 10 is not particularly limited. For example, in a case of disposing more than three collection containers, respective droplets may be guided to any one of the containers by presence or absence, and the size of electrical forces between the deflection plates 6, and may be collected.

<Operation>

Next, description will be given with respect to the microparticle fractionating apparatus 10 of the present embodiment. When fractionating microparticles by the microparticle fractionating apparatus 10 of the present embodiment, the sample liquid 21 and the sheath liquid 22 are introduced to the sample inlet and the sheath inlet respectively. Further, for example, in the charging electrode inlet, charges are given to the sheath liquid 22 by the first charging electrode 4. Thereafter, in the light radiation unit, detection of transmission flow speed of the microparticles and interval of the microparticles are performed at the same time when the optical characteristics of the microparticles are detected by the detection unit 3. The optical characteristics, the flow speed, and the interval of the detected microparticles are converted to electrical signals and then output to an entire control unit (not shown) of the apparatus.

The sample liquid 21 and the sheath liquid 22 which pass through the light radiation unit of the sample flow path 11 are discharged to the space outside of the microchip 1 from the orifice 12. At that time, the microchip 1 is vibrated by the vibration of the vibration 2 so that the microparticles are included one by one in the droplets D formed in the orifice 12.

Thereafter, the charges are given to the droplets D discharged from the orifice 12 at least at the BP (break-off-point) by the second charging electrode 5. At this time, a second voltage different from the first voltage applied to the first charging electrode 4 is applied to the second charging electrode 5. For example, as illustrated in FIG. 2A, while imbalance AC pulse signals are input to the voltage source 8 and the first voltage $V_1$ is applied to the first charging electrode 4, the second charging electrode 5 is connected to ground.

In this manner, it is possible to increase a capacitance C between the droplets D and a ground connection GND, which is obtained by the following Equation 1 by disposing the second charging electrode 5 to the BP (break-off-point) in which an amount of charge given to the droplets D is finally determined. Thus, it is possible to increase a charge amount Q given to the droplets D.

$$Q = C * V_1$$

Furthermore, since reference potential in charges is well-defined by disposing the second charging electrode 5 to the BP (break-off-point), fluctuation (external noise) effect of the ambient electric field decreases, and thus the charges amount Q given to the droplets D is stabilized. As a result, it is possible to improve blurring of the fluid stream during the fractionation and accurately sort the fluid stream to the collection containers 7a to 7c.

In addition, respective droplets D downstream from the BP (break-off-point) fall at predetermined intervals (distance $L_D$ between droplets), but there is a case where reaction force or attraction force occurs between the droplets D by the given charges. For example, as an ideal array state illustrated in FIG. 3A, in a case where the droplets are present on a straight line with no blurring in the traveling direction of the droplets D, the droplets are not affected by the charges. On the other hand, as illustrated in FIG. 3B, if the blurring occurs in the traveling direction of respective droplets D, the force is also generated in a vertical direction with respect to the traveling direction, and deviation width of the trajectory of respective droplets D increases.

In contrast, as the microparticle fractionating apparatus 10 of the present embodiment, if disposing the second charging electrode 5 to the BP (break-off-point), it is possible to lower intensity of the electric field emanating from the droplets D and decrease the reaction force and the attraction force acting between respective droplets D. As a result, as illustrated in FIG. 3C, it is possible to decrease the deviation width of the trajectory of the droplets D.

Moreover, a case of using the microchip 1 is described as an example in the above-described first embodiment, but the present technology is not limited thereto, and the same effect can be obtained even using a flow cell instead of the microchip 1. In addition, the light detection unit 3 can be re-disposed with an electrical or magnetic detector. In that case, fractionation may be performed by giving the charges to the droplets D in a similar manner, based on the magnetic characteristics or electrical characteristics of the microparticles.

Furthermore, in the microparticle fractionating apparatus described in PTLs 2 and 3, a ground electrode is disposed between the orifice and the deflection plate, however, since the electrode is intended to eliminate the influence of the high potential and the distance from the droplets D is long, it is not possible to increase the capacitance C between the droplets D. For this reason, it is difficult to obtain stability of the charge amount Q given to the droplets D or effect such as electric field decrease between respective droplets D.

2. Modified Example of First Embodiment

Next, description will be given with respect to the microparticle fractionating apparatus according to the modified example of the first embodiment of the present technology. FIG. 4 schematically illustrates the operation of the microparticle fractionating apparatus of the modified example of the first embodiment of the present technology. Moreover, in FIG. 4, the same reference numerals are used in the same ones as the configuration elements of microparticle fractionating apparatus of the first embodiment illustrated in FIG. 2A, and detailed description thereof will be omitted.

As illustrated in FIG. 4, in the microparticle fractionating apparatus of the present modified example, two voltage sources 8a and 8b are provided and apply opposite-phase voltages to the first charging electrode 4 and the second charging electrode voltage 5. Specifically, while non-inversion polarity AC pulse signals are input to the voltage source 8a and the first voltage $V_1$ is applied to the first charging electrode 4, the non-inversion polarity AC pulse signals are input to the voltage source 8b and the second voltage $V_2$ is applied to the second charging electrode 5.

A capacity between the droplets D at the BP (break-off-point) and the second charging electrode 5 doubles with respect to the configuration equivalently illustrated in FIG. 2A by providing the second charging electrode 5 in the vicinity of the BP (break-off-point) and applying the charges with phase opposite from the first charging electrode 4 to the second charging electrode 5. Thus, it is possible to give the same amount of voltage with half voltage of the above-described first embodiment. As a result, the voltages applied to the droplets D can be lower reducing the damages (risk) to cells.

In addition, in the microparticle fractionating apparatus of the present modified example, a voltage $V_1'$ in which a noise voltage $nu_n$ is superimposed on the voltages V1 directly applied to the droplets D by the first charging electrode 4, and a voltage $V_2'$ in which the $nu_n$ is superimposed on the voltage $V_2$ applied by the second charging electrode 5, are respectively expressed by the following equations 2 and 3.

$$V_1' = V_1 + nu_n$$
$$V_2' = V_2 + nu_n$$
$$= -V_1 + nu_n$$

Further, potential difference $V_g$ between the second charging electrode 5 and respective droplets D at the BP (break-off-point) is expressed by the following Equation 4. In other words, in the microparticle fractionating apparatus of the present modified example, since $V_n$, a noise component, is canceled, it is possible to decrease the influence of external noise.

$$V_g = V_1' - V_2'$$
$$= 2 * V_1$$

Moreover, other configurations, operations, and effects in the present modified example are the same as those of the above-described first embodiment.

3. Second Embodiment

Next, description will be given with respect to a microparticle fractionating apparatus of a second embodiment of the present technology. FIG. 5A schematically illustrates operation of the microparticle fractionating apparatus of the present embodiment, and FIG. 5B illustrates positional relation between a break-off-point and a second charging electrode. Moreover, in FIG. 5A and FIG. 5B, the same reference numerals are used in the same ones as the configuration elements of microparticle fractionating apparatus of the first embodiment illustrated FIG. 1, FIG. 2A and FIG. 2B, and detailed description thereof will be omitted.

As illustrated in FIG. 5A and FIG. 5B, in the microparticle fractionating apparatus of the present embodiment, the second charging electrode 15 is configured of a parallel plate electrode. In that case, the parallel plate electrode (second charging electrode 15) is opposed across the fluid stream 23, and disposed at a position that can give charges to the droplets D at least at the BP (break-off-point). In addition, voltage is applied to the second charging electrode 15 from the voltage source (not shown) so that the two plate electrodes have the same potential. Moreover, other configurations and operations in the present embodiment are the same as those of the above-described first embodiment.

As the microparticle fractionating apparatus of the present embodiment, also in a case of using the parallel plate electrode for the second charging electrode 15, since it is possible to stabilize the amount of the charges given to the droplets D, it is possible to realize stable sorting. Moreover, the parallel plate electrode used in the microparticle fractionating apparatus of the present embodiment, is not limited to the embodiment illustrated in FIG. 5A and FIG. 5B, for example, it is also possible to use an inverse C-shaped electrode as illustrated in FIG. 6A and FIG. 6B.

4. Third Embodiment

Next, description will be given with regard to the microparticle fractionating apparatus according to a third embodiment of the present technology. FIG. 7A schematically illustrates operation of a microparticle fractionating apparatus of the present embodiment, and FIG. 7B illustrates positional relation between a break-off-point and a second charging electrode. Moreover, in FIG. 7A and FIG. 7B, the same reference numerals are used in the same ones as the configuration elements of microparticle fractionating apparatus of the first embodiment illustrated in FIG. 1, FIG. 2A and FIG. 2B, and detailed description thereof will be omitted. In addition, FIG. 8A and FIG. 8B are plan views illustrating another embodiment of the second charging electrode.

As illustrated in FIG. 7A and FIG. 7B, in the microparticle fractionating apparatus of the present embodiment, a second charging electrode 25 is configured of a circular hole electrode. Moreover, a cylindrical electrode is illustrated in FIG. 7B, but the present technology is not limited thereto. For example, it is possible to use an electrode with a structure in which a circular hole is formed on a plate as illustrated in FIG. 8A and a substantially ring-shaped electrode in which a notch is formed in a portion as illustrated in FIG. 8B.

In this case, the circular hole electrode (second charging electrode 25) passes the fluid stream 23 through an inner bore and is disposed to apply charges to the droplets D at least at the BP (break-off-point). Moreover, other configurations and operations of the present embodiment are the same as those of the above-described first embodiments.

Also in the microparticle fractionating apparatus of the present embodiment, since the second charging electrode 25 giving charges to the droplets D at the BP (break-off-point) is provided, the amount of charge given to the droplets D becomes constant, and it is possible to stabilize the sorting.

In addition, it is possible that the present technology adopts the following configuration.

(1) A charging apparatus for charging droplets discharged from an orifice of a microparticle fractionating apparatus, the charging apparatus comprising:
a first electrode configured to apply a first bias from a bias source to a sample liquid supplying the orifice; and
a second electrode configured to apply a second bias from the bias source and referenced to the first bias to the droplets formed from the sample liquid, wherein the second electrode is located at a droplet break-off-point near the orifice.

(2) The charging apparatus of (1), wherein the second electrode is spaced less than or equal to 5 millimeters from the droplets at the droplet break-off-point.

(3) The charging apparatus of (1) or (2), wherein the second bias is at a ground potential of the bias source.

(4) The charging apparatus of (1) or (2), wherein the second bias has a potential opposite in phase to the first bias.

(5) The charging apparatus any of (1), (2) or (4), wherein the second bias has a value that is approximately equal in magnitude to the first bias.

(6) The charging apparatus of (5), wherein application of the second bias to the second electrode is configured to cancel a noise component of the bias source.

(7) The charging apparatus of (5) or (6), wherein application of the second bias to the second electrode is configured to substantially double an amount of charge in a droplet that was applied by the first electrode.

(8) The charging apparatus of any of (1)-(7), wherein a majority of the second electrode extends downstream of a droplet break-off-point.

(9) The charging apparatus of any of (1)-(8), wherein the second electrode is formed as at least one electrode plate.

(10) The charging apparatus of any of (1)-(8), wherein the second electrode is formed as a cylinder.

(11) The charging apparatus of any of (1)-(8), wherein the second electrode is formed as a hole in a plate.

(12) The charging apparatus of any of (1)-(8), wherein the second electrode is formed as a ring electrode.

(13) The charging apparatus of any of (1)-(12), further comprising a microchip in which the orifice is located; and a vibration device arranged to cause formation of the droplets.

(14) A method for charging droplets discharged from an orifice of a microparticle fractionating apparatus, the method comprising:
applying a first bias from a bias source to a first electrode arranged to be in contact with a sample liquid supplying the orifice that is arranged to produce the droplets;
referencing a second bias from the bias source to the first bias; and
applying the second bias to a second electrode located at a droplet break-off-point near the orifice.

(15) The method of (14), wherein the second electrode is spaced less than or equal to 5 millimeters from the droplets at the droplet break-off-point.

(16) The method of (14) or (15), wherein referencing the second bias from the bias source to the first bias comprises setting the second bias to a ground potential of the bias source.

(17) The method of (14) or (15), further comprising setting the second bias to have a value that is opposite in phase to the first bias.

(18) The method of (14), (15) or (17), further comprising applying the second bias to the second electrode to cancel a noise component of the bias source.

(19) The method of (14), (15), (17) or (18), further comprising applying the second bias at the second electrode so as to substantially double an amount of charge in a droplet that was applied by the first electrode.

(20) A microparticle fractionating apparatus comprising:
a droplet-forming device having an orifice and arranged to receive a sample liquid containing microparticles and produce a stream of separated droplets;
a first electrode configured to apply a first bias from a bias source to the sample liquid supplying the orifice;
a second electrode configured to apply a second bias from the bias source and referenced to the first bias to the separated droplets formed from the sample liquid, wherein the second electrode is located at a droplet break-off-point near the orifice; and
deflection plates located after the second electrode and arranged to subject the separated droplets to an electric field so as to deflect the paths of the separated droplets.

In addition, it is possible that the present technology adopts the following configuration.

(1) A microparticle fractionating apparatus includes a charging unit which gives charges to at least to a portion of droplets discharged from an orifice generating a fluid stream, in which the charging unit has first charging electrode that is disposed to be in contact with a sheath liquid and/or a sample liquid which flow through a flow path, and a first voltage is applied to a first charging electrode to give the charges to the sheath liquid and/or the sample liquid, and a second charging electrode in which a second voltage different from the first voltage is applied to give charges to the droplets at least at a position in which the liquid discharged from the orifice is made into droplets.

(2) The microparticle fractionating apparatus according to (1), in which the second charging electrode may give charges to the droplets from a position where the droplets are made to a position of 30 mm downstream in a travelling direction of the droplets.

(3) The microparticle fractionating apparatus according to (1) or (2), in which the second charging electrode is disposed at a position of less than 5 mm from the fluid stream.

(4) The microparticle fractionating apparatus according to any one of (1) to (3), in which the second charging electrode is a plate electrode, or a parallel plate electrode, or a circular hole electrode.

(5) The microparticle fractionating apparatus according to any one of (1) to (4), in which the second charging electrode is a ground electrode.

(6) The microparticle fractionating apparatus according to any one of (1) to (4), in which opposite-phase voltages are applied to the first charging electrode and the second charging electrode.

(7) The microparticle fractionating apparatus according to any one of (1) to (6), in which pulse voltages are applied to the first charging electrode and/or the second charging electrode.

(8) The microparticle fractionating apparatus according to any one of (1) to (7), in which the first charging electrode is disposed so as to be in contact with a sheath flow.

(9) The microparticle fractionating apparatus according to any one of (1) to (8), in which the orifice is formed in a replaceable microchip, and the first charging electrode is disposed in a sheath liquid flow path provided in the microchip.

(10) The microparticle fractionating apparatus according to any one of (1) to (9), in which a deflection plate which changes a traveling direction of the droplets downstream from the second charging electrode is provided.

(11) The microparticle fractionating apparatus according to (10), in which the deflection plate is opposed across the fluid stream.

(12) A method of fractionating microparticles includes giving charges to a sheath liquid and/or a sample liquid which flow through a flow path by applying a first voltage to a first charging electrode; and giving charges to the droplets at a position in which a liquid discharged from an orifice generating at least a fluid stream turns into droplets by applying a second voltage different from the first voltage to a second charging electrode.

(13) The method of fractionating microparticles according to (12), in which the second charging electrode is a ground electrode.

(14) The method of fractionating microparticles according to (12), in which opposite-phase voltages are applied to the first charging electrode and the second charging electrode.

(15) The method of fractionating microparticles according to any one of (12) to (14), in which pulse voltages are applied to the first charging electrode and/or the second charging electrode.

The present disclosure contains subject matter related to that disclosed in Japanese Priority Patent Application JP 2012-246432 filed in the Japan Patent Office on Nov. 8, 2012, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

1 MICROCHIP
2 VIBRATION DEVICE
3 LIGHT DETECTION UNIT
4, 5, 15, 25 CHARGING ELECTRODE
6 DEFLECTION PLATE
7a to 7c COLLECTION CONTAINER
8, 8a, 8b VOLTAGE SOURCE
10 MICROPARTICLE FRACTIONATING APPARATUS
11 SAMPLE FLUID PATH
12 ORIFICE
21 SAMPLE LIQUID
22 SHEATH LIQUID
23 FLUID STREAM
BP BREAK-OFF-POINT
D DROPLET
$L_D$ DISTANCE BETWEEN DROPLETS

The invention claimed is:

1. A charging apparatus for charging droplets discharged from an orifice of a microparticle fractionating apparatus, the charging apparatus comprising:
a first electrode configured to apply a first bias from a bias source to a sample liquid supplying the orifice; and
a second electrode and circuit configured to apply a second bias other than ground potential and referenced to the first bias to the droplets formed from the sample liquid, wherein the second electrode is spaced less than or equal to 5 millimeters from a droplet break-off-point in a fluid stream discharged into air from the orifice.

2. The charging apparatus of claim 1, wherein the second electrode extends at least 30 millimeters downstream from the droplet break-off-point.

3. The charging apparatus of claim 1, wherein the second bias has a potential opposite in phase to the first bias.

4. The charging apparatus of claim 1, wherein the second bias has a value that is approximately equal in magnitude to the first bias.

5. The charging apparatus of claim 4, wherein application of the second bias to the second electrode is configured to cancel a noise component of the bias source.

6. The charging apparatus of claim 4, wherein application of the second bias to the second electrode is configured to substantially double an amount of charge in a droplet that was applied by the first electrode.

7. The charging apparatus of claim 1, wherein a majority of the second electrode extends downstream of a droplet break-off-point.

8. The charging apparatus of claim 7, wherein the second electrode is formed as at least one electrode plate.

9. The charging apparatus of claim 7, wherein the second electrode is formed as a cylinder.

10. The charging apparatus of claim 7, wherein the second electrode is formed as a hole in a plate.

11. The charging apparatus of claim 7, wherein the second electrode is formed as a ring electrode.

12. The charging apparatus of claim 1, further comprising: a microchip in which the orifice is located; and a vibration device arranged to cause formation of the droplets.

13. A method for charging droplets discharged from an orifice of a microparticle fractionating apparatus, the method comprising:
    applying a first bias from a bias source to a first electrode arranged to be in contact with a sample liquid supplying the orifice that is arranged to produce the droplets;
    referencing a second bias to the first bias; and
    applying the second bias other than ground potential to a second electrode spaced less than or equal to 5 millimeters from a droplet break-off-point in a fluid stream discharged into air from the orifice.

14. The method of claim 13, wherein the second electrode extends at least 30 millimeters downstream from the droplet break-off-point.

15. The method of claim 13, further comprising setting the second bias to have a value that is opposite in phase to the first bias.

16. The method of claim 15, further comprising applying the second bias to the second electrode to cancel a noise component of the bias source.

17. The method of claim 13, further comprising applying the second bias at the second electrode so as to substantially double an amount of charge in a droplet that was applied by the first electrode.

18. A microparticle fractionating apparatus comprising:
    a droplet-forming device having an orifice and arranged to receive a sample liquid containing microparticles and produce a stream of separated droplets;
    a first electrode configured to apply a first bias from a bias source to the sample liquid supplying the orifice;
    a second electrode and circuit configured to apply a second bias other than ground potential and referenced to the first bias to the separated droplets formed from the sample liquid, wherein the second electrode is spaced less than or equal to 5 millimeters from a droplet break-off-point in a fluid stream discharged into air from the orifice; and
    deflection plates located after the second electrode and arranged to subject the separated droplets to an electric field so as to deflect the paths of the separated droplets.

* * * * *